United States Patent
Iyer

(10) Patent No.: US 10,111,617 B2
(45) Date of Patent: Oct. 30, 2018

(54) SYSTEMS AND METHODS FOR EEG MONITORING

(71) Applicant: COVIDIEN LP, Mansfield, MA (US)

(72) Inventor: Darshan Ramesh Iyer, Superior, CO (US)

(73) Assignee: Covidien LP, Mansfield, MA (US)

( * ) Notice: Subject to any disclaimer, the term of this patent is extended or adjusted under 35 U.S.C. 154(b) by 393 days.

(21) Appl. No.: 14/858,160

(22) Filed: Sep. 18, 2015

(65) Prior Publication Data
US 2016/0081617 A1 Mar. 24, 2016

Related U.S. Application Data

(60) Provisional application No. 62/053,558, filed on Sep. 22, 2014.

(51) Int. Cl.
*A61B 5/04* (2006.01)
*A61B 5/00* (2006.01)
*A61B 5/0476* (2006.01)

(52) U.S. Cl.
CPC .......... *A61B 5/4821* (2013.01); *A61B 5/0476* (2013.01); *A61B 5/6814* (2013.01); *A61B 5/742* (2013.01); *A61B 5/748* (2013.01); *A61B 5/04004* (2013.01); *A61B 5/04012* (2013.01); *A61B 5/4094* (2013.01); *A61B 2562/046* (2013.01)

(58) Field of Classification Search
USPC ........................................................ 600/544
See application file for complete search history.

(56) References Cited

U.S. PATENT DOCUMENTS

| | | | | |
|---|---|---|---|---|
| 4,201,224 A | * | 5/1980 | John | A61B 5/0476 600/544 |
| 4,907,597 A | * | 3/1990 | Chamoun | A61B 5/048 600/544 |
| 5,305,746 A | | 4/1994 | Fendrock | |
| 5,458,117 A | | 10/1995 | Chamoun et al. | |
| 6,032,064 A | | 2/2000 | Devlin et al. | |
| 6,728,564 B2 | | 4/2004 | Lähteenmäki | |
| 7,054,453 B2 | | 5/2006 | Causevic et al. | |
| 7,054,454 B2 | | 5/2006 | Causevic et al. | |
| 7,072,705 B2 | | 7/2006 | Miga et al. | |
| 7,367,949 B2 | | 5/2008 | Korhonen et al. | |
| 7,398,115 B2 | | 7/2008 | Lynn | |

(Continued)

OTHER PUBLICATIONS

Dahaba et al., Bispectral Index (BIS) monitoring of acute encephalitis with refractory, repetitive partial seizures, Minerva Anesesiol., Apr. 2010; 76(4): 298-301.*

(Continued)

*Primary Examiner* — Jacqueline Cheng
*Assistant Examiner* — Tho Tran
(74) *Attorney, Agent, or Firm* — Fletcher Yoder PC

(57) ABSTRACT

A patient monitoring system includes an electroencephalography (EEG) monitor and an EEG sensor array. The EEG sensor array includes a plurality of electrodes configured to acquire EEG signals from a patient. The EEG monitor may be configured to calculate one or more depth of anesthesia indices for the patient based on received EEG signals from the EEG sensor array. Additionally, the EEG monitor may be configured to generate and display a topographic color map of the calculated depth of anesthesia indices.

21 Claims, 9 Drawing Sheets

(56) References Cited

U.S. PATENT DOCUMENTS

| | | | |
|---|---|---|---|
| 7,407,485 B2 | 8/2008 | Huiku | |
| 7,447,541 B2 | 11/2008 | Huiku et al. | |
| 2003/0093004 A1* | 5/2003 | Sosa | A61B 5/04 600/544 |
| 2004/0163648 A1 | 8/2004 | Burton | |
| 2004/0243017 A1 | 12/2004 | Causevic | |
| 2005/0113704 A1 | 5/2005 | Lawson et al. | |
| 2006/0217614 A1 | 9/2006 | Takala et al. | |
| 2007/0010723 A1 | 1/2007 | Uutela et al. | |
| 2007/0167694 A1 | 7/2007 | Causevic et al. | |
| 2007/0249954 A1* | 10/2007 | Virag | A61B 5/02405 600/544 |
| 2008/0139908 A1 | 6/2008 | Kurth | |
| 2008/0167540 A1 | 7/2008 | Korhonen et al. | |
| 2008/0208073 A1* | 8/2008 | Causevic | A61B 5/048 600/544 |
| 2008/0243021 A1 | 10/2008 | Causevic et al. | |
| 2009/0290772 A1* | 11/2009 | Avinash | G06F 19/3487 382/130 |
| 2011/0053859 A1* | 3/2011 | Deadwyler | A61K 38/22 514/18.1 |
| 2014/0187973 A1* | 7/2014 | Brown | A61B 5/0476 600/483 |

OTHER PUBLICATIONS

Darshan Iyer, George Zouridakis; "Topographic Phase Maps Using Interative Independent Component Analysis"; ICASSP 2011.

Peng Wen; "Consciousness, EEG and depth of anaesthesia"; Australian College of Physical Scientists and Engineers in Medicine 2012.

* cited by examiner

SYSTEMS AND METHODS FOR EEG MONITORING

CROSS-REFERENCE TO RELATED APPLICATION

This application claims priority to U.S. Provisional Application No. 62/053,558, filed Sep. 22, 2014, the disclosure of which is hereby incorporated by reference in its entirety.

BACKGROUND

The present disclosure relates generally to medical devices and, more particularly, to sensors for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring certain physiological characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as electroencephalography (EEG), and the devices built based upon electroencephalographic techniques are commonly referred to as EEG monitors. EEG monitors use non-invasive electrophysiological monitoring to evaluate global changes in a patient's condition, for example, during surgical procedures. Examples of global changes may include assessing the effects of anesthetics, evaluating asymmetric activity between the left and right hemispheres of the brain in order to detect cerebral ischemia, and detecting burst suppression. Certain techniques analyze EEG signals using various algorithms to measure the level of consciousness of a patient's during general anesthesia.

EEG measurements are captured using EEG monitoring devices, and sensors associated with these monitoring devices are applied to the patient. Typically, the sensors include electrodes that may be applied to various sites on the patient (e.g., the temple and/or forehead). For example, certain EEG sensors may include a substrate that includes several electrodes for placement on the forehead to noninvasively acquire an EEG signal.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As noted above, sensors including electrodes may be used in conjunction with EEG monitoring devices to capture EEG measurements, such as depth of anesthesia measurements. For example, sensors for EEG monitoring may include electrodes for placement on the forehead to noninvasively acquire an EEG signal. However, an EEG signal may be noisy in the presence of artifacts, such as eye blinks, eye movements, muscle activity, or electrical interference, which may adversely affect the determination of the EEG measurements. Additionally, clinically adverse events, such as seizures and/or ischemic events, may be undetected via localized EEG monitoring. That is, depending on the location of the electrodes, an EEG sensor may be unable to distinguish between normal anesthetized patients and patients undergoing clinically adverse events.

Accordingly, the present disclosure is generally related to techniques for increasing the specificity and resolution (e.g., spatial and/or temporal) of depth of anesthesia measurements. For example, an EEG sensor array may be used to acquire one or more EEG signals from a patient from locations distributed about the patient's head. In some embodiments, an EEG sensor array may be used in conjunction with the present techniques to acquire one or more EEG signals from the patient. An EEG monitor may be configured to receive the EEG signals to calculate a depth of anesthesia index (e.g., depth of anesthesia value) for each electrode or for selected electrodes of the EEG sensor array. In some embodiments, the EEG monitor may be configured to generate a topographic depth of anesthesia color map illustrating a spatial distribution of depth of anesthesia values relative to the patient's head. Further, the EEG monitor may be configured to monitor EEG signals and/or depth of anesthesia values for one or more locations of the patient's head over time to detect clinically adverse events, such as seizures and/or ischemia.

Figure 1:
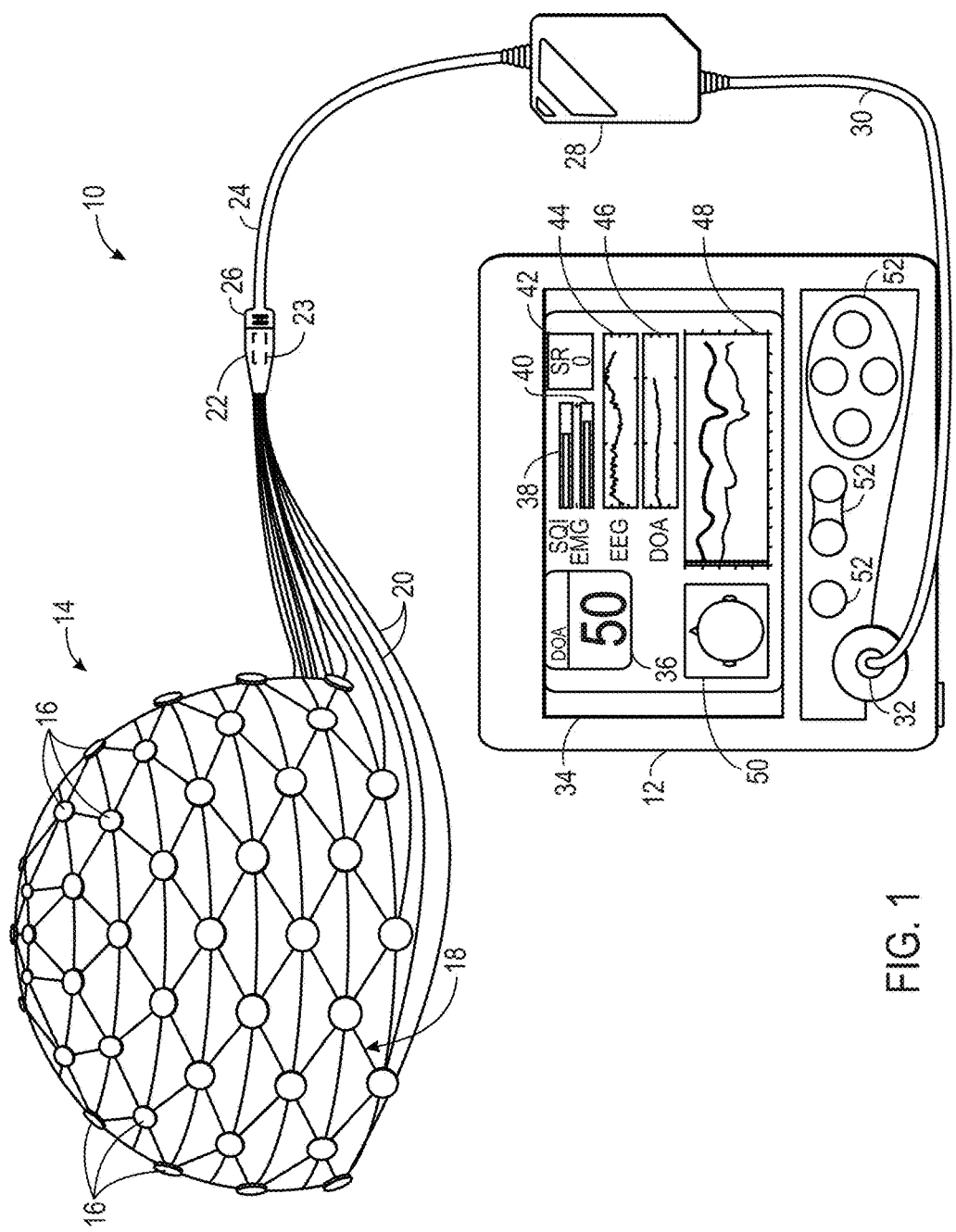
FIG. 1 is a schematic diagram of a patient monitoring system including an EEG monitor and an EEG sensor array, in accordance with an embodiment.

FIG. 1 illustrates an embodiment of a patient monitoring system 10 including an electroencephalography (EEG) monitor 12 that may be used in conjunction with an EEG sensor array 14. The EEG sensor array 14 includes a plurality of electrodes 16 that are used to acquire one or more EEG signals from a patient, which may be used by the monitor 12 to determine one of more physiological characteristics of the patient. For example, the monitor 12 may be configured to determine a depth of anesthesia (DOA) measure (e.g., depth of anesthesia index or value), such as a BISPECTRAL™ (BIS™) index, based on the one or more EEG signals from the plurality of electrodes 16.

The electrodes 16 may be formed from any suitable conductive material or materials to enable the electrodes to perform electrical measurements on the patient. In some embodiments, the electrodes 16 may be formed from flexible conductive materials, such as one or more conductive inks, to provide enhanced flexibility and conformance to patient tissue. It should be understood that the EEG sensor array 14 may include additional components and/or materials, such as one or more structural layers, foam layers, adhesive layers, sponges, conductive gels, etc. Additionally, in some embodiments, the EEG sensor array 14 may be configured for a one-time use and may be discarded after use by one patient. In other embodiments, the EEG sensor array 14 may be reusable or at least partially reusable.

The electrodes 16 may be supported by a framework 18, which may be configured to facilitate proper placement of the electrodes 16 on a patient's head. The framework 18 may flexible (e.g., elastic), semi-rigid, or rigid, and may be formed of any suitable materials. In certain embodiments, the framework 18 may enable the electrodes 16 to be placed on the patient's head without scalp preparation (e.g., shaving) or abrasion. In one embodiment, the framework 18 may be a Geodesic Sensor Net. Further, in some embodiments, different sized frameworks 18 may be constructed to accommodate different sized patients (e.g., neonatal, pediatric, or adult). In other embodiments, the framework 18 may be one-size fits all or may include adjustment features to adjust the framework 18 to fit about the patient's head. Additionally, the framework 18 may include indicia to facilitate the proper placement of the framework 18 and electrodes 16 about the patient's head. For example, the indicia include text, numbers, graphics, symbols, and/or changes in color that may provide information to a caregiver regarding the proper placement of the framework 18 and electrodes 16 about the patient's head.

As noted above, it may be desirable to utilize an EEG sensor array 14 to increase the specificity and the resolution (e.g. spatial and/or temporal) of the depth of anesthesia measurements. Accordingly, in some embodiments, the EEG sensor array 14 may include between 6 electrodes 16 and 500 electrodes 16. In certain embodiments, the EEG sensor array 14 may include between 64 electrodes 16 and 256 electrodes 16. Each electrode 16 may be coupled to a respective lead 20 (e.g., a conductor, channel, etc.), which may be configured to transmit signals to and/or from a respective electrode 16. It should be noted that the illustrated embodiment does not show a lead 20 coupled to each electrode 16, and a few representative leads 20 have been illustrated. In certain embodiments, the EEG sensor array 14 may include a connector 22, such as a paddle connector, which may be configured to receive the plurality of leads 20. In certain embodiments, the connector 22 may include a memory device 23, which may be configured to store information about the EEG sensor array 14, such as the number of electrodes 16 of the EEG sensor array 14, the type or model of the EEG sensor array 14, calibration data related to the electrodes 16 (e.g., a range of acceptable impedance values), which may be provided to the monitor 12. It should be appreciated that the location of the memory device 23 is not limited to the connector 22, and the memory device 23 may be disposed in alternate location in other embodiments.

The connector 22 may be coupled to a cable 24 (e.g., a patient interface cable) via a connector 26. The cable 24 may be coupled to a digital signal converter 28. As will be described in more detail below, the digital signal converter 28 receives, filters, and processes the EEG signals for each channel (e.g., each lead 20). The digital signal converter 28 is coupled to a cable 30, which may be coupled to the monitor 12 via a port 32. In certain embodiments, the digital signal converter 28 may be embedded in the monitor 12. However, it may be desirable to provide the digital signal converter 28 external to the monitor 12 such that the digital signal converter 28 may be closer to the patient's head where the EEG signals may be subject to less interference from other medical equipment.

The monitor 12 may be configured to calculate physiological characteristics relating to one or more EEG signals received from the EEG sensor array 14. For example, the monitor 12 may be configured to algorithmically calculate an EEG parameter, such as a depth of anesthesia index (e.g., a depth of anesthesia value) from the EEG signal. In certain embodiments, the depth of anesthesia index may be determined using spontaneous EEG signals. That is, in certain embodiments, the depth of anesthesia index may not be determined using evoked potentials (e.g., in response to a stimulus). Additionally, in certain embodiments, the depth of anesthesia index may be determined based at least in part upon a bispectral analysis of the EEG signals. In some embodiments, the depth of anesthesia index may be a BISPECTRAL™ index (e.g., a BIS™ value), which may be determined using the methods and algorithms discussed in U.S. Pat. No. 5,458,117, which is hereby incorporated by reference for all purposes as if fully set forth herein. BIS™ is a measure of a patient's level of consciousness during general anesthesia. In certain embodiments, the monitor 12 may calculate a depth of anesthesia index for each electrode 16 (e.g., channel) or may calculate a depth of anesthesia index using EEG signals acquired from two or more selected electrodes (e.g., from a region of interest). In one embodiment, the monitor 12 may calculate a depth of anesthesia index based on depth of anesthesia indices from one or more regions of the patient's head. Additionally, as will be described in more detail below, the monitor 12 may be configured to monitor the EEG signals and/or the depth of anesthesia indices for particular regions of interest, such as the quadrants of the patient's head. For example, the monitor 12 may be configured to analyze the correlation between the depth of anesthesia indices for each region of interest. In one embodiment, the monitor 12 may analyze the correlation between the depth of anesthesia indices for each region of interest over time (e.g., during anesthesia) to detect clinically adverse events. Still further, as will be described in more detail below, the monitor 12 may be configured to analyze the correlation for each frequency band of the EEG signals to detect clinically adverse events.

The monitor 12 may also include a display 34 configured to display physiological characteristics, historical trends of physiological characteristics, other information about the system, and/or alarm indications. For example, the monitor 12 may display one or more anesthesia indices (e.g., depth of anesthesia indices) of the patient, such as a depth of anesthesia (DOA) value 36. In some embodiments, as will be described in more detail below, the display 34 may display an anesthesia index (e.g., the DOA value 36) for each desired region of the patient's head. The DOA value 36 may represent a dimensionless number (e.g., ranging from 0, i.e., silence, to 100, i.e., fully awake and alert) output from a multivariate discriminant analysis that quantifies the overall bispectral properties (e.g., frequency, power, and phase) of the EEG signal. For example, a DOA value 36 between 40 and 60 may indicate an appropriate level for general anesthesia.

The monitor 12 may also display a signal quality index (SQI) bar graph 38 (e.g., ranging from 0 to 100) which measures the signal quality of the EEG channel source(s) (e.g., the electrode(s) 16 used to acquire the EEG signal) based on impedance data, artifacts, and other variables. In certain embodiments, the monitor 12 may also display an electromyograph (EMG) bar graph 40 (e.g., ranging from 30 to 55 decibels) which indicates the power (e.g., in decibels) in the frequency range of 70 to 110 Hz. The frequency range may include power from muscle activity and other high-frequency artifacts. The monitor 12 may further display a suppression ratio (SR) 42 (e.g., ranging from 0 to 100 percent), which represents the percentage of epochs over a given time period (e.g., the past 63 seconds) in which the EEG signal is considered suppressed (i.e., low activity). In certain embodiments, the monitor 12 may also display a burst count for the number of EEG bursts per minute, where a "burst" is defined as a short period of EEG activity preceded and followed by periods of inactivity or suppression.

Additionally, the monitor 12 may display one or more EEG waveforms 44. For example, the monitor 12 may receive one or more EEG signals from one or more electrodes 16 and may display the EEG waveform 44 for each received EEG signal. In certain embodiments, the EEG waveform 42 may be filtered. Additionally, as will be described in more detail below, the monitor 12 may display one or more depth of anesthesia waveforms 46. The monitor 12 may also display trends 48 over a certain time period (e.g., one hour) for EEG, DOA, SR, EMG, SQI, and/or other parameters. In certain embodiments, the monitor 12 may display stepwise instructions for placing the EEG sensor array 14 on the patient and/or an image illustrating the proper placement of the EEG sensor array 14 on a patient's head. Further, as will be described in more detail below, the monitor 12 may display one or more topographical color maps 50 of the EEG activity of the patient's head.

Additionally, the monitor 12 may include various control inputs 52 (e.g., buttons and switches) to facilitate management and operation of the monitor 12. For example, the monitor 12 may include function keys, a power switch, adjustment buttons, an alarm silence button, and so forth. The control inputs 52 may enable a user to select or input a specific sensor type or model, such as the specific number of electrodes 16 of the EEG sensor array 14. This may enable the monitor 12 to select the appropriate instructions for analyzing the EEG signals and calculating the anesthesia indices (e.g., depth of anesthesia indices) based on the particular EEG sensor array 14. Further, in some embodiments, the control inputs 52 may enable a user to select electrode(s) 16 of interest to monitor the EEG signals and/or depth of anesthesia indices from selected electrode(s) or groups of electrodes.

Figure 2:
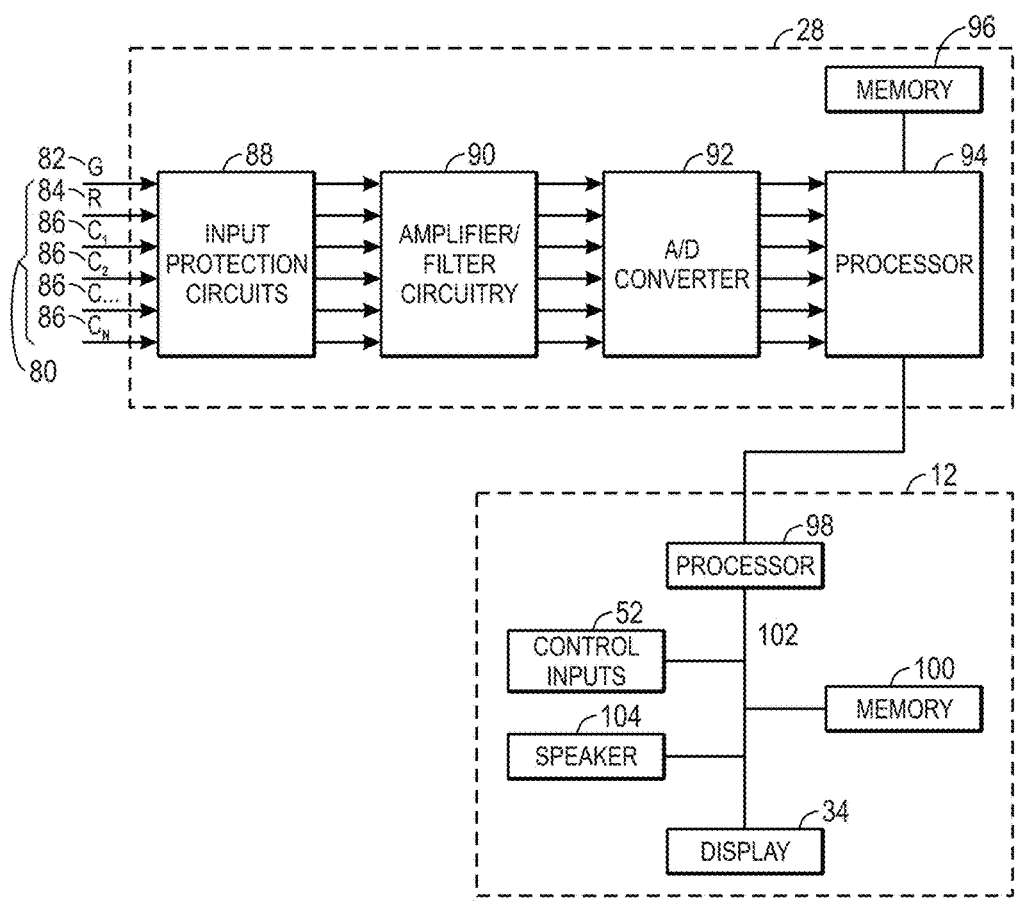
FIG. 2 is a block diagram of the patient monitoring system of FIG. 1, in accordance with an embodiment.

One embodiment of the various components of the digital signal converter 28 and the monitor 12 is illustrated with respect to FIG. 2. While the illustrated embodiment is directed toward a digital signal converter 28 that is external to the monitor 12, it should be appreciated that, in other embodiments, the digital signal converter 28 may be integrated into the monitor 12. As illustrated, the digital signal converter 28 is configured to receive a plurality of EEG signals 80 from the EEG sensor array 14. The digital signal converter 28 is configured to receive at least three EEG signals 80 to calculate a depth of anesthesia index of the patient. In particular, the digital signal converter 28 may receive a ground signal 82 from a ground electrode of the EEG sensor array 14, a reference signal 84 from a reference electrode of the EEG sensor array 14, and one or more sensing signals 86 from one or more sensing electrodes of the EEG sensing array 14. In certain embodiments, the reference electrode may be positioned about the center of the top of the patient's head. Further, in some embodiments, one or more of the sensing signals 86 may be used to monitor artifacts from muscular movements, such as eye blinking or movement. As will be described in more detail below, the monitor 12 may be configured to select certain electrodes of the EEG sensor array 14 to monitor specific regions of the patient's head. Further, the monitor 12 may be configured to select which electrodes are to be used for monitoring artifacts and which electrodes are to be used for monitoring physiological characteristics of the patient.

In certain embodiments, the digital signal converter 28 and/or the monitor 12 may include one or more input protection circuits 88 to filter the EEG signals 80 and may include amplifier/filter circuitry 90 to remove DC and high frequency components. Additional components of the digital signal converter 28 and/or the monitor 12 may include one or more analog-to-digital (A/D) converters 92, a processor 94, and a memory 96 (e.g., RAM, ROM, flash memory, etc.) coupled to the processor 94, which may be configured to store instructions that may be read and executed by the processor 94 to implement the present techniques. The monitor 12 may be configured to send signals to and/or receive signals from the digital signal converter 28. In some embodiments, the monitor 12 may receive calculated physiological characteristics from the processor 94. In other embodiments, the monitor 12 may receive digitized signals from the one or more A/D converters 92 or filtered digitized signals from the processor 94. The monitor 12 may also include one or more memory devices 100 (e.g., a RAM and/or a ROM) coupled to the processor 98 by an internal bus 102. The one or more memory devices 100 may be configured to store instructions that may be read and executed by the processor 98 to implement the present techniques. In certain embodiments, the monitor 12 may store instructions that are specific to a particular sensor type or model. For example, the monitor 12 may store a plurality of instructions for analyzing EEG signals and calculating depth of anesthesia indices and may select a particular set of instructions from the memory 100 based on the number of electrodes 16 of the EEG sensor array 14. The monitor 12 may also include the display 34, the control inputs 52, and a speaker 104 coupled to the internal bus 102.

As noted above, the monitor 12 may be configured to dynamically select which electrodes 16 of the EEG sensor array 14 to use for the calculation of the depth of anesthesia index. The memory 100 of the monitor 12 may store one or more default settings for the electrodes 16 to be used, which may be determined and selected based on at least in part upon the type of EEG sensor array 14 (e.g., the number of electrodes 16 in the EEG sensor array 14), information relating to the patient, surgical procedure, and/or anesthetics used with the patient, and/or input provided by the caregiver. The monitor 12 may be configured to adjust the selected default setting or select a new default setting (i.e., to select one or more different electrodes 16 or only a subset of the available electrodes 16) in response to a determination that the EEG signal may contain artifacts. For example, one or more of the sensing signals 86 may be used by the monitor 12 to monitor artifacts, and the monitor 12 may determine that artifacts are present in a sensing signal 86. Accordingly, the monitor 12 may be configured to select a different electrode 16 to use to monitor the patient's EEG and to calculate the depth of anesthesia index. It should be appreciated that the monitor 12 may dynamically cycle between the electrodes 16 of the EEG sensor array 14 until a desired signal quality is reached. In one embodiment, in an implementation in which specific regions of the head are being monitored and compared to one another, the monitor 12 may provide instructions to cycle through the electrodes 16 in one or more quadrants to find either satisfactory or the best signal quality within an individual quadrant.

In some embodiments, a user may be configured to input the desired electrodes 16 (e.g., for a region of interest) using one or more of the control inputs 52. For example, the electrodes 16 of the EEG sensor array 14 may be labeled (e.g., numerically, alphabetically, or a combination thereof) and the user may be configured to input the corresponding label for the desired electrodes 16 via the control inputs 52. To facilitate the selection, the display 40 may be configured to display a graphical representation of the EEG sensor array 14. In certain embodiments, the monitor 12 may be configured to download information from the memory 23 of the EEG sensor array 14 to provide the monitor 12 with information regarding the type of EEG sensor array 14, such as the number of electrodes 16. This information may be used by the monitor 12 to create a graphical representation of the specific EEG sensory array 14 or to select a graphical representation of the specific sensor array 14 from a set of graphical representations for various EEG sensor arrays 14.

Figure 3:
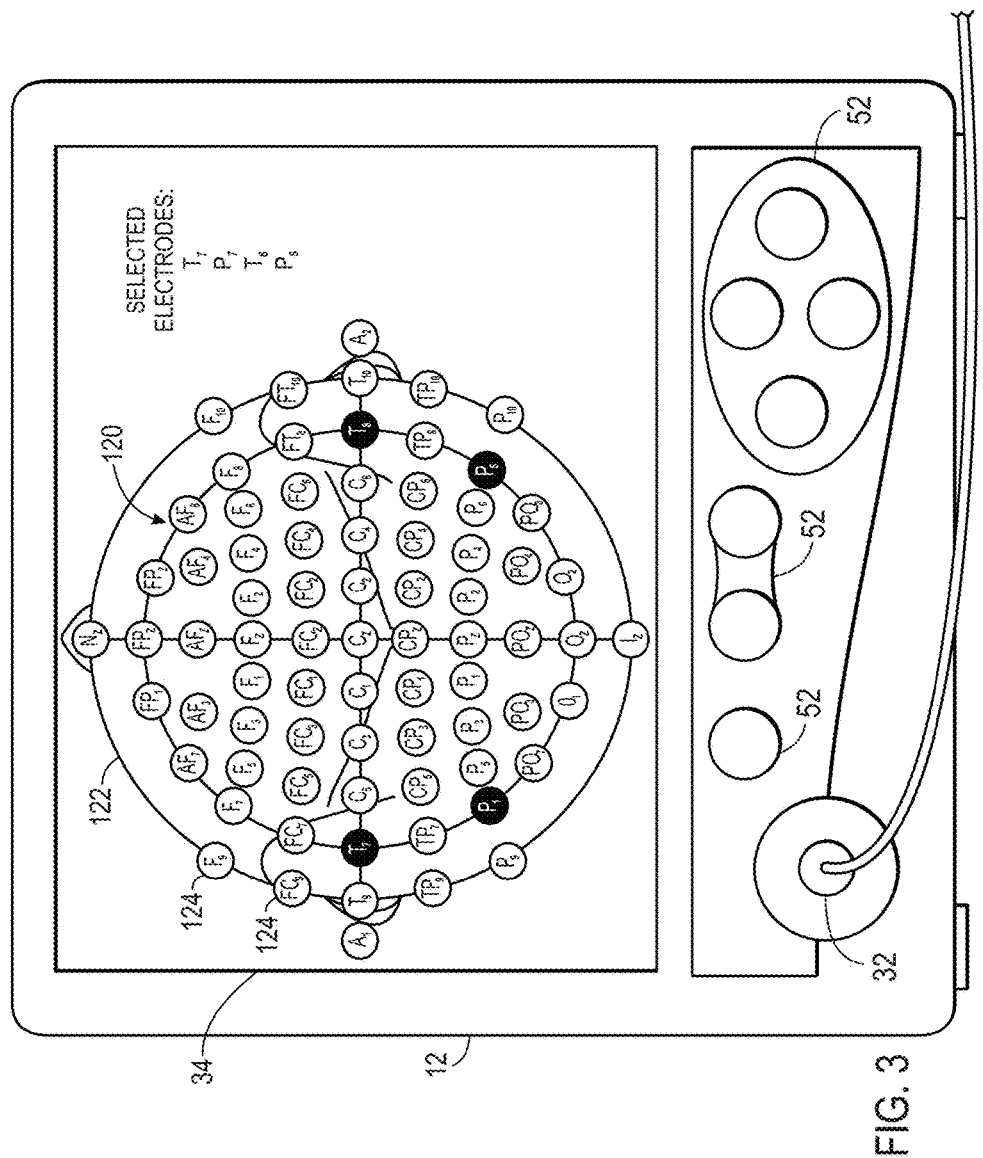
FIG. 3 is a schematic diagram of a display of the EEG monitor of FIG. 1 illustrating a graphical illustration of the EEG sensor array of FIG. 1, in accordance with an embodiment.

As illustrated in FIG. 3, the display 34 may display a graphical representation 120 of the EEG sensor array 14 and graphical representation 122 of a patient's head. Providing the graphical representation 122 of the patient's head may be desirable to facilitate a caregiver in quickly selecting the desired electrodes 16 based upon one or more regions of interest of the patient's head. In certain embodiments, the display 34 may also be configured to display labels 124 (e.g., numerical, alphabetical, or a combination thereof) for each electrode 16 or for selected electrodes 16. It should be appreciated that the labels 124 may be provided in any suitable form. For example, in one embodiment, the labels 124 may be disposed proximate to the respective electrode 16.

Figure 4:
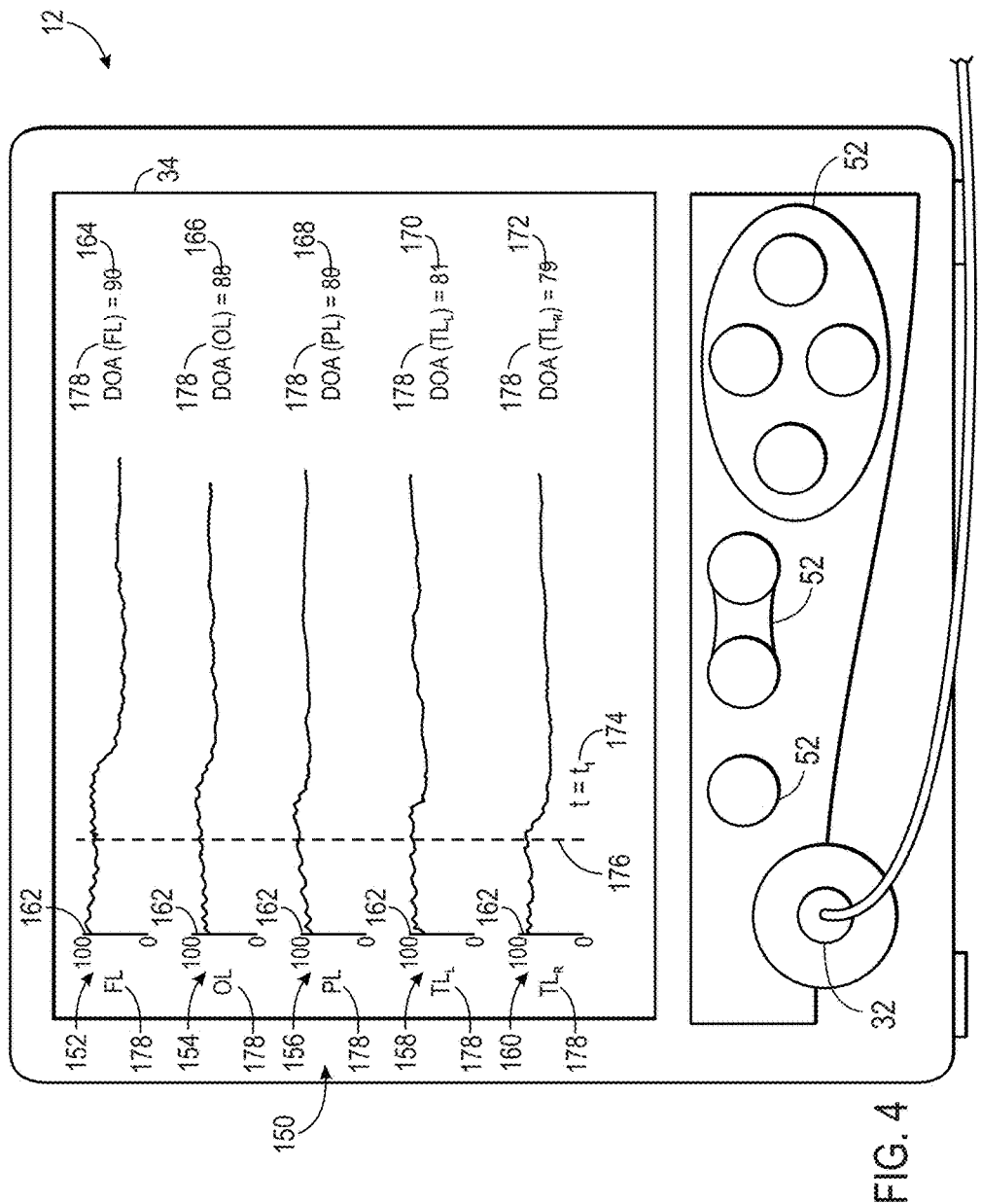
FIG. 4 is a schematic diagram of a display of the EEG monitor of FIG. 1 illustrating a plurality of depth of anesthesia index waveforms, in accordance with an embodiment.

As noted above, the monitor 12 may be configured to calculate an anesthesia index (e.g., depth of anesthesia index) for each sensing electrode, for each selected sensing electrodes, or for a group of selected electrodes. For example, FIG. 4 illustrates an embodiment of the display 34 displaying a plurality of depth of anesthesia waveforms 150. In the illustrated embodiment, the depth of anesthesia waveforms 150 are representative of the depth of anesthesia (DOA) index for the lobes of the patient's brain (e.g., frontal, occipital, parietal, and temporal). However, it should be appreciated that any number of depth of anesthesia waveforms 150 may be displayed for any suitable region of the patient's head. For example, in other embodiments, the display 34 may display a depth of anesthesia waveform for each hemisphere or quadrant of the patient's head. In other embodiments, the display 34 may display a depth of anesthesia waveform for each sensing electrode of the EEG sensor array 14 or for selected sensing electrodes of the EEG sensor array 14.

As illustrated, the depth of anesthesia waveforms 150 include a first depth of anesthesia waveform 152 illustrating the depth of anesthesia index of the frontal lobe of the patient over time. Additionally, the depth of anesthesia waveforms 150 include a second depth of anesthesia waveform 154 illustrating the depth of anesthesia index for the occipital lobe of the patient over time and a third waveform 156 illustrating the depth of anesthesia index of the parietal lobe of the patient over time. Further, the depth of anesthesia waveforms 150 include fourth and fifth depth of anesthesia waveforms 158 and 160 illustrating the depth of anesthesia indices of the temporal lobe of the patient over time. In particular, the fourth depth of anesthesia waveform 158 illustrates depth of anesthesia index of the temporal lobe of the left hemisphere of the patient and the fifth waveform 160 illustrates depth of anesthesia index of the temporal lobe of the right hemisphere of the patient. Each depth of anesthesia waveform 150 includes a y-axis 162 showing the range in depth of anesthesia indices from 0 to 100.

In certain embodiments, the depth of anesthesia index for each depth of anesthesia waveform 150 may be calculated using a selected channel (e.g., a selected sensing electrode 16 from the EEG sensor array 14) from the respective lobe of the patient's brain. The selected channel may be selected by the user (e.g., via the control inputs 52 and/or the display 34), by the monitor 12, or a combination thereof. For example, if the monitor 12 determines that the user-selected channel is noisy, the monitor 12 may select a different channel proximate to the user-selected channel. In other embodiments, the depth of anesthesia indices for each depth of anesthesia waveform 150 may be calculated using two or more channels from the respective lobe of the patient's brain. For example, the EEG signals from the two or more channels may be combined to determine a single depth of anesthesia index. In other embodiments, a depth of anesthesia index may be determined for each channel of the two or more channels, and the depth of anesthesia indices may be combined (e.g., averaged) to determine a single depth of anesthesia index.

In addition to the depth of anesthesia waveforms 150, the display 34 may also display depth of anesthesia indices 36 for each desired region (e.g., the lobes of the patient's brain). For example, as illustrated, the display 34 may display a depth of anesthesia index value 164 for the frontal lobe, a depth of anesthesia index 166 for the occipital lobe, a depth of anesthesia index 168 for the parietal lobe, a depth of anesthesia index 170 for the left temporal lobe, and a depth of anesthesia index 172 for the right temporal lobe. The depth of anesthesia index of a particular region may be determined by selecting the depth of anesthesia index calculated from one or more electrode signals of electrodes associated with that region. For example, the depth of anesthesia index of the desired lobe or hemisphere may be an average of all of the depth of anesthesia indices from all active electrodes associated with those regions or may be an average of only those depth of anesthesia indices that are above a quality threshold. Alternatively, the depth of anesthesia index of a particular region may be the depth of anesthesia index based on a single representative electrode signal. In certain embodiments, the display 34 may update the depth of anesthesia indices continuously over time. In one embodiment, the display 34 may be configured to display the depth of anesthesia index for each desired region at a particular time point, which may be user-selected. For example, a user may select a time point, such as $t_1$ 174, and the display 34 may be configured to display the depth of anesthesia index of each depth of anesthesia index waveform 150 at the selected time point. Additionally, the display 34 may display a line 176, or another indicator, on each depth of anesthesia index waveform 150 at the selected time point.

In some embodiments, the monitor 12 may also display one or more indicators 178 to provide identifying information for each displayed depth of anesthesia index and/or depth of anesthesia index waveform. For example, the indicators 178 may provide information relating to the region of interest for which the depth of anesthesia index was determined and/or the one or more electrodes 16 that were used to acquire the EEG signal to calculate the respective depth of anesthesia index. In certain embodiments, the indicators 178 may include text, symbols, graphics, and/or images. As illustrated, the indicators 178 may include letters corresponding to the lobe of the brain from which the depth of anesthesia index was determined, such as "FL" for frontal lobe, "OC" for occipital lobe, "PL" for parietal lobe, "$TL_L$" for left temporal lobe, and "$TL_R$" for right temporal lobe. In other embodiments, the indicators 187 may include letters corresponding to the quadrant or hemisphere of the brain from which the depth of anesthesia index was determined.

As illustrated by the depth of anesthesia index waveforms 152, 154, 156, 158, and 160 and the DOA indices 164, 166, 168, 170, and 172, the depth of anesthesia index may vary between the different lobes of the patient. Providing the depth of anesthesia waveforms and the depth of anesthesia indices for various locations about the patient's head may facilitate the caregiver in administering an optimal amount of anesthesia to the patient and/or detecting clinically adverse events. The depth of anesthesia index waveform may have a specific signature as the depth of anesthesia increases and decreases while the patient goes under and emerges from anesthesia. The caregiver may monitor the depth of anesthesia index waveforms during anesthesia to determine if the depth of anesthesia index waveforms are similar to the expected signature of the depth of anesthesia index. Further, the caregiver may compare the depth of anesthesia index waveforms for the different regions of the patient's head to determine if the correlation between the depth of anesthesia index waveforms is indicative of normal activity under anesthesia or is indicative of a clinically adverse event, such as ischemia or a seizure. For example, a seizure may result in a localized region of high EEG activity (e.g., a high depth of anesthesia index). Thus, if one of the depth of anesthesia indices 164, 166, 168, 170, or 172 is higher than the other depth of anesthesia indices by a predetermined threshold, the caregiver may determine that the patient is having a seizure. Additionally, ischemic events may cause derivations from normal depth of anesthesia index patterns. For example, an ischemic event may cause one side (e.g., hemisphere) of the patient's head to be more active (e.g., have a higher depth of anesthesia index) than the other side (e.g., hemisphere) of the patient's head. Accordingly, the caregiver may determine that the patient is undergoing an ischemic event if the depth of anesthesia indices from one side of the patient's head (e.g., the DOA index 170) is greater than the depth of anesthesia indices from the other side of the patient's head (e.g., the DOA index 172).

Figure 5:
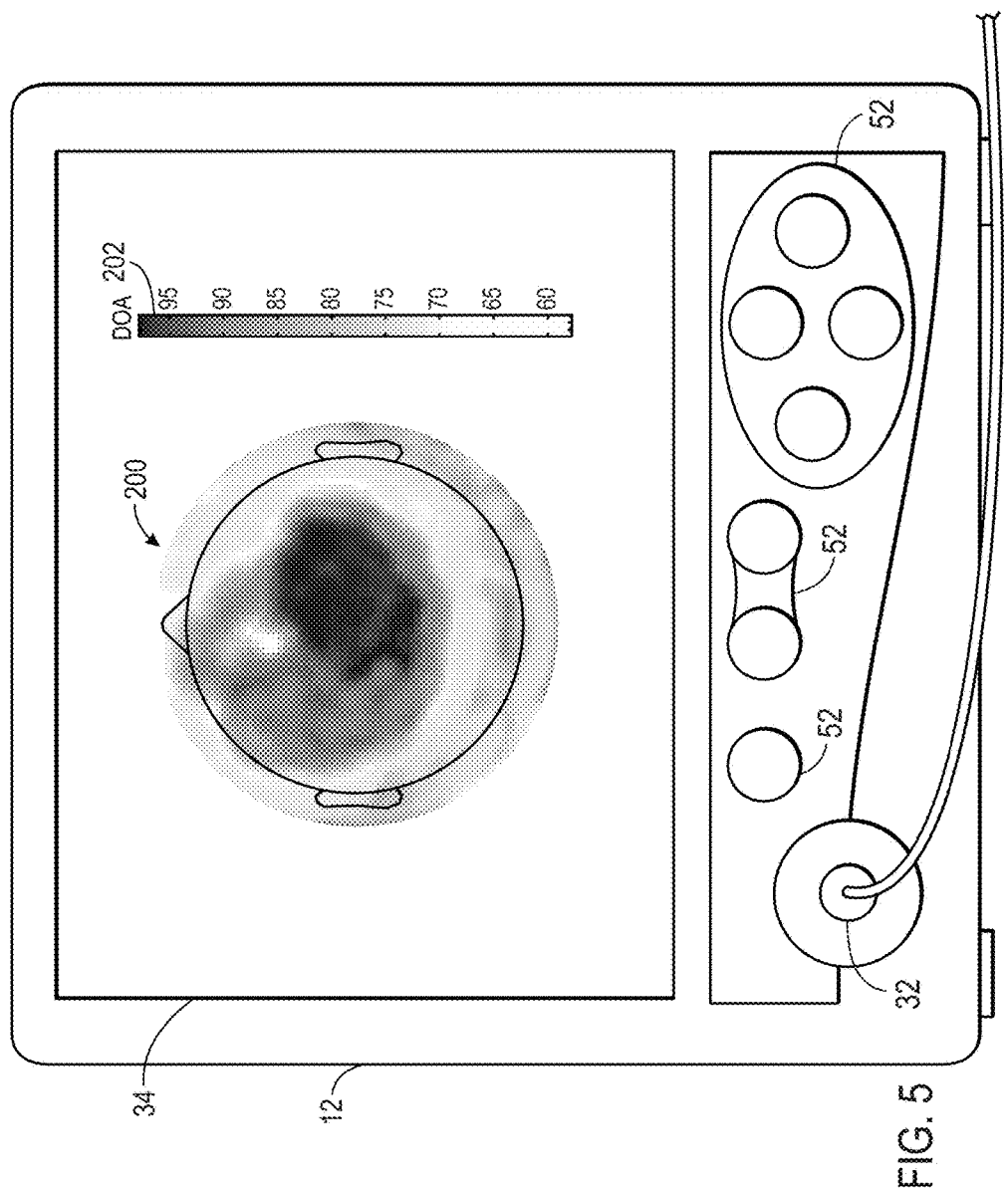
FIG. 5 is a schematic diagram of a display of the EEG monitor of FIG. 1 illustrating a topographical depth of anesthesia color map, in accordance with an embodiment.
Figure 6:
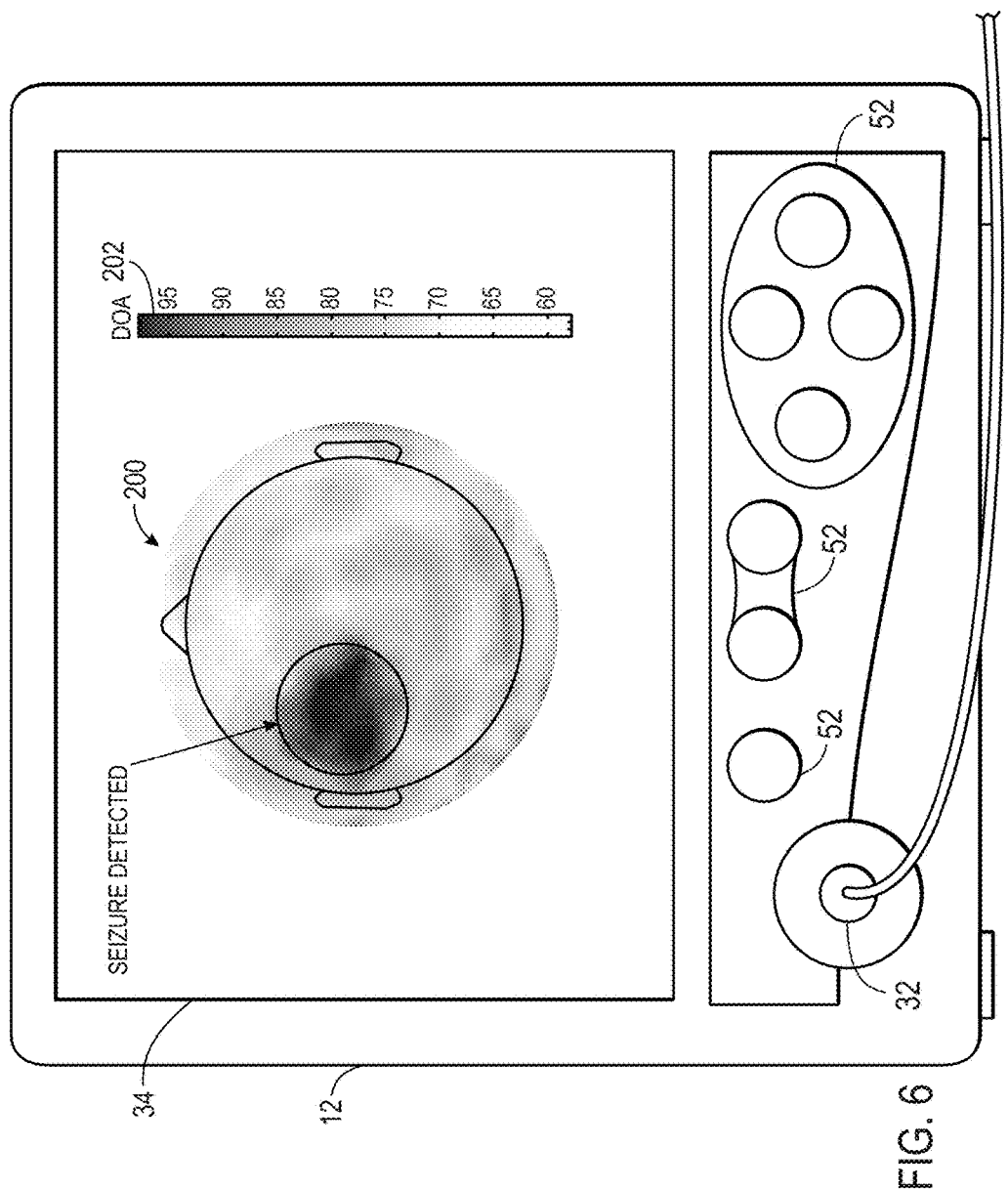
FIG. 6 is a schematic diagram of a display of the EEG monitor of FIG. 1 illustrating a topographical depth of anesthesia color map and an indication of a clinically adverse event, in accordance with an embodiment.

To further facilitate the caregiver in administering an optimal amount of anesthesia to the patient and/or detecting clinically adverse events, the monitor 12 may also be configured to generate and display a topographic depth of anesthesia color map 200 of the patient's entire head (e.g., both hemispheres of the patient's head), as illustrated in FIG. 5. The color map 200 includes a scale 202 defining the relationship between the colors and the depth of anesthesia indices. As illustrated, high EEG activity and high depth of anesthesia indices, such as a depth of anesthesia index of 80 or greater, are represented by dark colors (e.g., black and/or dark grays), while low EEG activity and low depth of anesthesia indices, such as depth of anesthesia index of 80 or less, are represented by lighter colors (e.g., medium grays, light grays, and/or white). While the illustrated embodiment is a black and white embodiment of the color map 200 and associated scale 202, it should be appreciated that the present techniques may be implemented using any other suitable colors. For example, in one embodiment, the scale 202 may range from red for high depth of anesthesia indices to blue for low depth of anesthesia indices. In particular, the scale 202 may transition between dark red, light red, orange, yellow, green, light blue, and dark blue as the depth of anesthesia indices decrease. Thus, the present embodiments are not limited to a black and white color scheme or a monochromatic color scheme, and certain embodiments may include a multi-chromatic color scheme.

The monitor 12 may be configured to continuously or periodically update the color map 200. Further, in some embodiments, the monitor 12 may be configured to store the color maps 200 for a surgical procedure as historical data to enable the caregiver to review the color maps 200 at a later time. Additionally, the monitor 12 may be configured to provide the color map 200 at a user-specified time point, which may be entered using the control inputs 52.

The color map 200 may enable the caregiver to quickly determine areas of high EEG activity (e.g., high depth of anesthesia indices) and areas of low EEG activity (e.g., low depth of anesthesia indices). This may facilitate the caregiver in administering the correct dosage of anesthesia, monitoring the progression of the anesthesia, and detecting clinically adverse events. In particular, the EEG activity of the patient may be high when the patient initially receives anesthesia and may decrease (e.g., to a depth of anesthesia index between 40 and 60) as the patient goes under anesthesia. Additionally, the correlation of the EEG activity between the quadrants of the patient's head may be high (e.g., the EEG activity may be similar through the quadrants of the patient's head) when the patient initially receives anesthesia. As the patient goes under anesthesia, the correlation of the EEG activity between the quadrants may decrease and the intranetworking activity changes. These changes may not be captured by a bilateral or unilateral sensor. For example, as the patient goes under anesthesia, the front quadrants of the patient's head may decrease in EEG activity faster than the back of the patient's head, and as the patient is brought out of anesthesia, the EEG activity of the back quadrants of the patient's head may increase in EEG activity faster than the front quadrants of the patient's head.

Further, as noted above, a seizure may result in a localized region of high EEG activity (e.g., a high depth of anesthesia index). The topographical color map 200 may enable the caregiver to quickly identify any potential localized regions of high EEG activity. As noted above, a unilateral EEG sensor and a bilateral EEG sensor do not provide EEG information for the entirety of the patient's head. As such, the unilateral and bilateral EEG sensors may not capture EEG activity associated with a seizure. Thus, by providing EEG information for the entirety of the patient's head, the present techniques may facilitate the detection of a seizure.

Additionally, ischemic events may cause one side (e.g., hemisphere) of the patient's head to be more active (e.g., have a higher depth of anesthesia index) than the other side (e.g., hemisphere) of the patient's head. The topographical color map 200 and depth of anesthesia indices for the hemispheres or quadrants of the patient's head may enable the caregiver to quickly identify patterns of EEG activity indicative of ischemic events. While a bilateral EEG sensor may provide EEG information for the front quadrants of the patient's head, the EEG activity for the back quadrants of the patient's head is unknown. Providing EEG activity for the entirety of the patient's head may enable the caregiver to more quickly and accurately detect ischemic events, as well as distinguish between early and late anesthesia. By way of example, the EEG activity captured by a bilateral EEG sensor may indicate that the front left quadrant of the patient's head is significantly more active than the front right quadrant. However, given this information, the caregiver may not be able to quickly and accurately determine whether the patient is experiencing an ischemic event or a seizure, and the caregiver may not be able to distinguish between early and late anesthesia. Thus, the present techniques may be advantageous over techniques using a unilateral or a bilateral EEG sensor.

Figure 7:
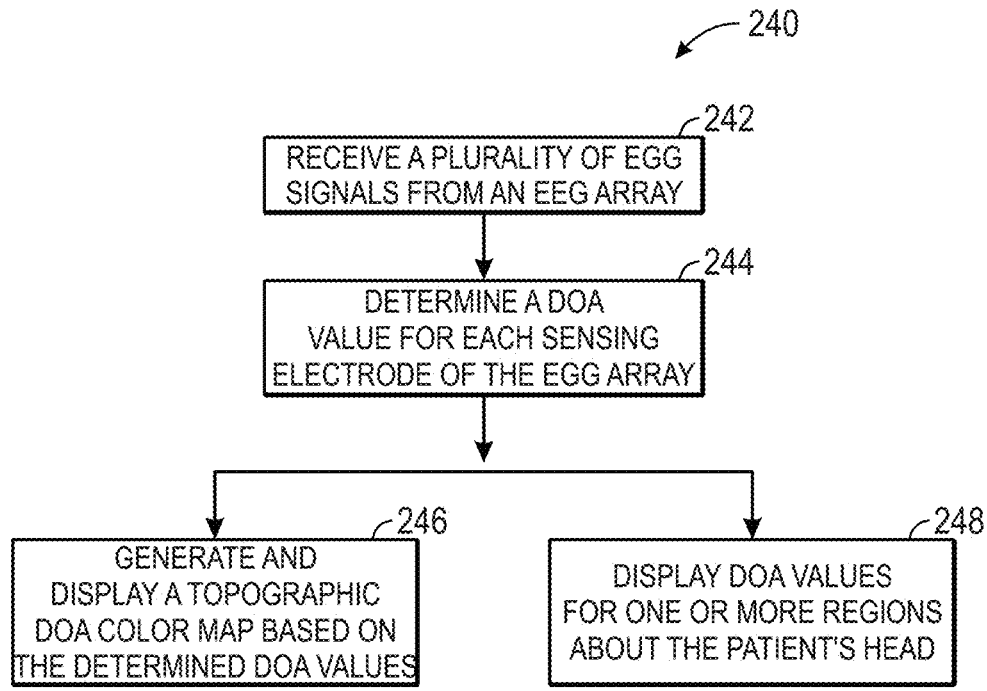
FIG. 7 is a process flow diagram of a method for determining and displaying depth of anesthesia values and a depth of anesthesia color map, in accordance with an embodiment.

Additionally, the present embodiments provide various methods for determining and displaying depth of anesthesia indices and a depth of anesthesia color map. For example, FIG. 7 illustrates a method 240 for determining and depth of anesthesia indices (e.g., depth of anesthesia values) and/or a depth of anesthesia color map. The method 240 may be performed as an automated procedure by a system, such as the system 10. In addition, certain steps of the method may be performed by a processor, such as the processor 94 of the digital signal converter and/or the processor 98 of the monitor 12, or by a processor-based device, such as the digital signal converter 28 and/or the monitor 12, that includes instructions for implementing certain steps of the method 240. Further, certain steps or portions of the method 240 may be performed by separate devices (e.g., by the EEG sensor array 14, the digital signal converter 28, and/or the monitor 12).

The method 240 may include receiving a plurality of EEG signals from an EEG sensor array (e.g., the EEG sensor array 14) (block 242). As noted above, the EEG sensor array 14 may include a ground electrode, a reference electrode, and a plurality of sensing electrodes. The method 240 may also include determining a depth of anesthesia value for each sensing electrode of the EEG sensor array (block 244). As noted above, the depth of anesthesia values may be calculated by the processor 94 of the digital signal converter 28 and/or by the processor 98 of the monitor 12. Additionally, the method 240 may include generating and displaying a topographic depth of anesthesia color map for the patient's head based at least in part upon the calculated depth of anesthesia values of the EEG sensor array (block 246). For example, the monitor 12 may determine the location of each depth of anesthesia value relative to the patient's head based on the electrode of the EEG sensor array 14 from which the depth of anesthesia value was determined. The monitor 12 may then assign a color to each depth of anesthesia value based on a predetermined color scale (e.g., the scale 202). Additionally, in some embodiments, the method 240 may include displaying a depth of anesthesia value and/or a depth of anesthesia waveform for one or more regions about the patient's head (block 248). For example, the one or more regions may include the frontal lobe, the occipital lobe, the parietal lobe, the left temporal lobe, and the right temporal lobe. In other embodiments, the one or more regions may include the quadrants of the patient's head. In some embodiments, the one or more regions may be user-selected.

While the topographical color map 200 may be visually interpreted by a caregiver, in some embodiments, the method 240 may include detecting a clinical condition of the patient based at least in part upon the depth of anesthesia color map. Detecting a clinical condition, such as a healthy or normal, a seizure or ischemia, may include identifying one or more features and/or patterns of EEG activity in the depth of anesthesia color map that are indicative of the clinical condition. For example, identifying the one or more features and/or patterns may include pattern matching (e.g., comparing the depth of anesthesia color map to a plurality of stored depth of anesthesia color maps that include features and/or patterns of EEG activity that are indicative of a clinical condition). In response to detecting the clinical condition, the method 240 may include providing an indication of a detected clinical condition.

Figure 8:
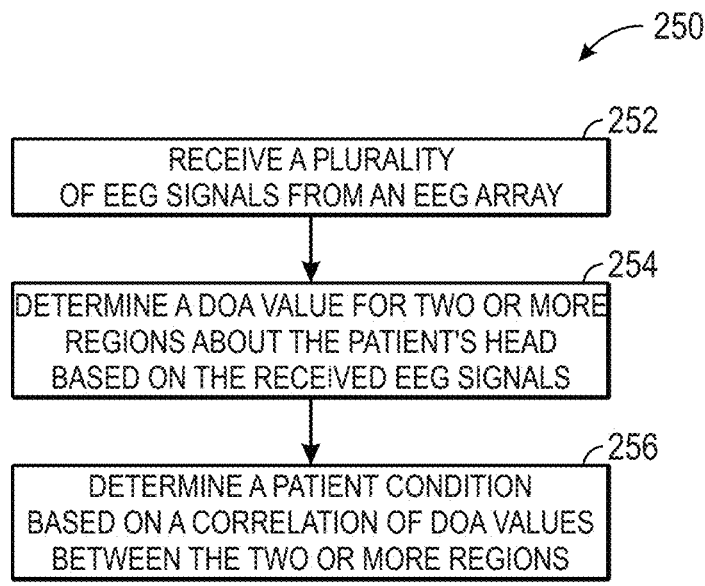
FIG. 8 is a process flow diagram of a method for determining a patient condition based on a correlation of depth of anesthesia values between regions of a patient's head, in accordance with an embodiment.

The present embodiments also provide various methods for determining a patient condition (e.g., a clinically adverse event) based on the EEG activity of the patient. For example, FIG. 8 illustrates a method 250 for determining a patient condition. The method 250 includes receiving a plurality of EEG signals from an EEG sensor array (e.g., the EEG sensor array 14) (block 252). The method 250 also includes determining a depth of anesthesia value for two or more regions of a patient's head based on the received EEG signals (block 254). In some embodiments, a depth of anesthesia value may be determined for each quadrant of the patient's head. In other embodiments, a depth of anesthesia value may be determined for each sensing electrode of the EEG sensor array. Additionally, the method 250 includes determining a patient condition based on a correlation between the depth of anesthesia values of the two or more regions (block 256). The correlation may be determined in the time domain or the frequency domain. The patient condition may correspond to a healthy patient (e.g., having normal or expected EEG activity during anesthesia) or a patient experiencing a clinically adverse event, such as a seizure or ischemia.

Figure 9:
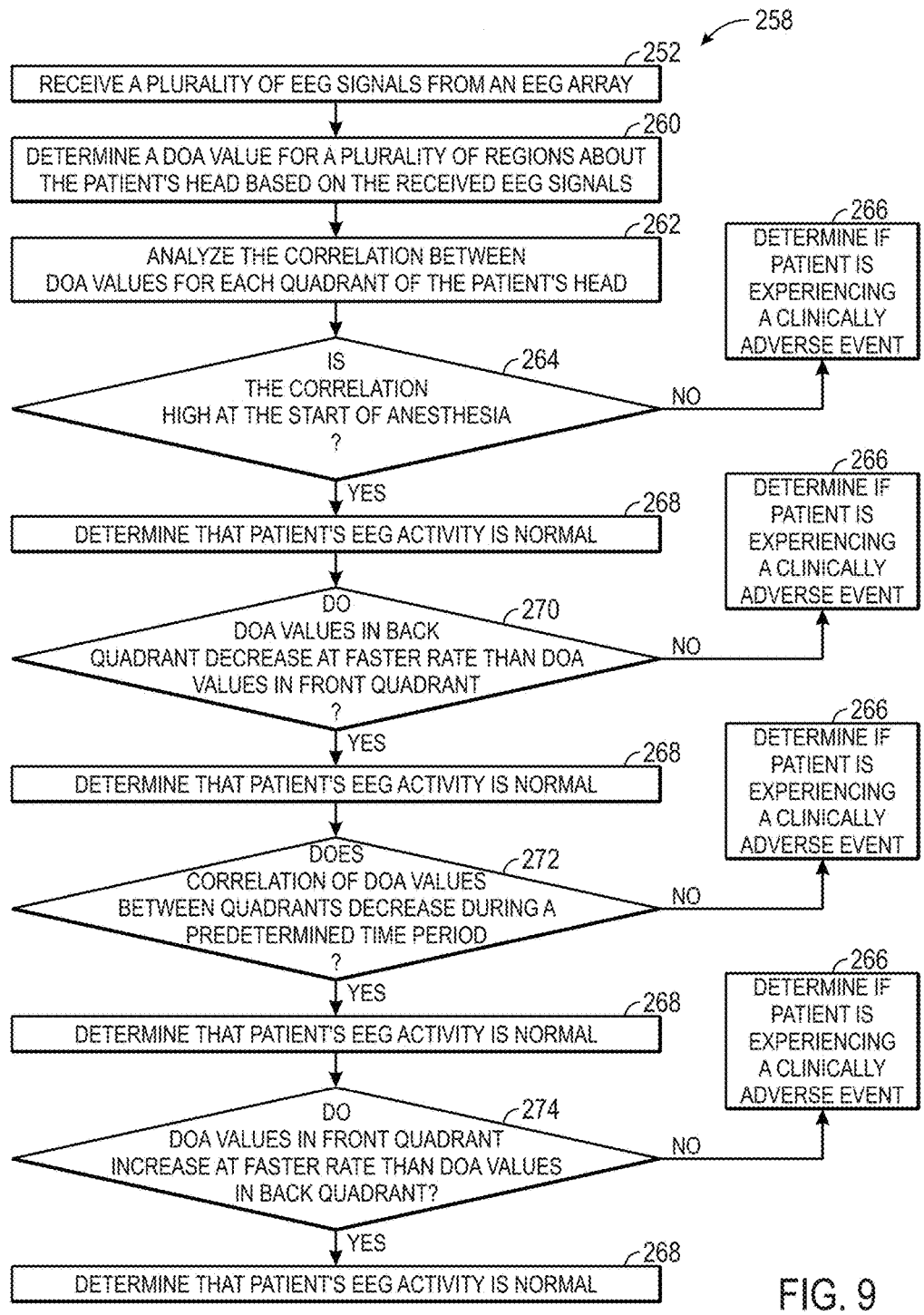
FIG. 9 is a process flow diagram of a method for determining whether a patient's EEG activity is normal based on a correlation of depth of anesthesia values between quadrants of the patient's head, in accordance with an embodiment.

FIG. 9 illustrates an embodiment of a method 258 for determining if the patient's EEG activity is expected or normal during anesthesia. The method 258 may include receiving a plurality of EEG signals from an EEG sensor array (e.g., the EEG sensor array 14) (block 252). The method 250 also includes determining a depth of anesthesia value for a plurality of regions of a patient's head based on the received EEG signals (block 260). In some embodiments, a depth of anesthesia value may be determined for each quadrant of the patient's head. In other embodiments, a depth of anesthesia value may be determined for each sensing electrode of the EEG sensor array.

The method 258 also includes analyzing the correlation between depth of anesthesia values for each quadrant of the patient's head (block 262). In some embodiments, analyzing the correlation between depth of anesthesia values for each quadrant may include determining a correlation coefficient (e.g., the linear correlation or Pearson's r) between the quadrants. The correlation coefficient is a dimensionless value ranging from −1 to 1. It should be appreciated that because the correlation coefficient is determined for a pair of variables, a correlation coefficient may be determined for each pair of quadrants (e.g., between the front left quadrant (FL) and the front right quadrant (FR), between FL and the back right quadrant (BR), between FL and the back left quadrant (BL), between FR and BR, between FR and BL, and between BR and BL). Accordingly, six correlation coefficients may be determined when the correlation of depth of anesthesia values between the quadrants is analyzed.

Additionally, the method 258 may include determining whether the correlation of depth of anesthesia values between the quadrants at the start of anesthesia is high (block 264). In some embodiments, determining whether the correlation is high may include determining whether the correlation coefficients are above a predetermined threshold. The predetermined threshold may be between 0 and 1. In one embodiment, the predetermined threshold may be between 0.5 and 1. If the correlation of depth of anesthesia values between the quadrants at the start of anesthesia is not high, the method 258 may include determining if the patient is experiencing a clinically adverse event (block 266), which will be described in more detail below with respect to FIG. 10. In response to determining that the correlation at the start of anesthesia is high, it may be determined that the patient's EEG activity is normal or expected (block 268).

The method 258 may also include determining whether the depth of anesthesia values in the front quadrants decrease at a faster rate than the depth of anesthesia values in the back quadrants (block 270). As noted above, as the patient goes under anesthesia (e.g., after a predetermined time has elapsed from when the anesthesia is delivered to the patient), the EEG activity in the back quadrants may decrease at a faster rate than the EEG activity in the front quadrants. Accordingly, the rate of change of the depth of anesthesia values for the front quadrants and back quadrants may be determined. If the rate of change of the depth of anesthesia values in the back quadrants is not greater than the rate of change of the depth of anesthesia values in the front quadrants by a predetermined threshold, the method 258 may include determining if the patient is experiencing a clinically adverse event (block 266). If the rate of change of the depth of anesthesia values in the back quadrants is greater than the rate of change of the depth of anesthesia values in the front quadrants by the predetermined threshold, it may be determined that the patient's EEG activity is normal or expected (block 268).

The method 258 may also include determining whether the correlation of depth of anesthesia values between the quadrants decreases during a predetermined time period from the initiation of anesthesia delivery (block 272). As noted above, the correlation between quadrants may decrease as the patient goes under anesthesia. Accordingly, if the correlation does not decrease, the method 258 may include determining if the patient is experiencing a clinically adverse event (block 266). If the correlation of depth of anesthesia values between quadrants decreases during the predetermined time, it may be determined that the patient's EEG activity is normal or expected (block 268).

Further, the method 258 may include determining whether the depth of anesthesia values in the front quadrants increase at a faster rate than the depth of anesthesia values in the back quadrants as the patient is brought out of anesthesia (block 274). As the patient comes out of anesthesia, the EEG activity in the front quadrants may increase at a faster rate than the EEG activity in the back quadrants. If the rate of change of the depth of anesthesia values in the front quadrants is not greater than the rate of change of the depth of anesthesia values in the back quadrants by a predetermined threshold, the method 258 may include determining if the patient is experiencing a clinically adverse event (block 266). If the rate of change of the depth of anesthesia values in the front quadrants is greater than the rate of change of the depth of anesthesia values in the back quadrants by the predetermined threshold, it may be determined that the patient's EEG activity is normal or expected (block 268).

Figure 10:
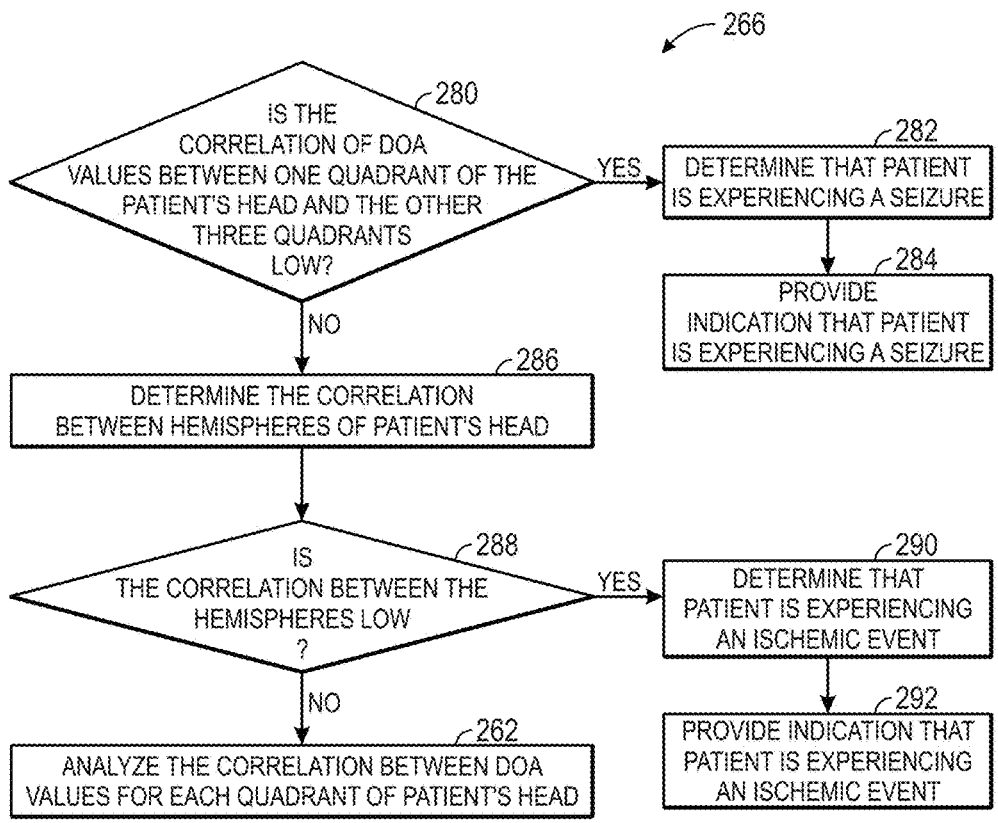
FIG. 10 is a process flow diagram of a method for determining whether a patient is experiencing a clinically adverse event based on a correlation of depth of anesthesia values between quadrants of the patient's head, in accordance with an embodiment.

FIG. 10 illustrates a method 266 for determining whether the patient is experiencing a clinically adverse event. The method 266 includes determining whether the correlation of depth of anesthesia values between one quadrant and the other three quadrants is low (block 280). In particular, determining whether the correlation of depth of anesthesia values between one quadrant and the other three quadrants is low may include determining whether the correlation between the one quadrant and the other three quadrants differs from the correlation of depth of anesthesia values between the other three quadrants by a predetermined threshold. For example, if the correlation between FL and FR, between FL and BR, and between FL and BL is less than the correlation between FR and BR, FR and BL, and BR and BL by a predetermined threshold, it may be determined that the correlation for FL is low. Low correlation between one quadrant and the other three quadrants may be indicative of a localized region of high EEG activity (e.g., high EEG activity in the one quadrant), which may indicate that the patient is experiencing a seizure. Accordingly, the method 266 may include determining that the patient is experiencing a seizure in response to determining that the correlation of depth of anesthesia values between one quadrant and the other three quadrants is low (block 282). In some embodiments, the method 266 may additionally include determining if there is a localized region of high depth of anesthesia values to facilitate the determining that the patient is experiencing a seizure. Further, the method 266 may include providing an indication that the patient may be experiencing a seizure (block 284).

If the correlation of depth of anesthesia values between one quadrant and the other three quadrants is not low, the method 266 may include determining the correlation between the hemispheres of the patient's head (block 286). Determining the correlation between the hemispheres may include determining a correlation coefficient (e.g., the linear correlation or Pearson's r) between the hemispheres. The method 266 also includes determining whether the correlation between the hemispheres is low (block 288). In some embodiments, it may be determined that the correlation is low if the correlation is less than a predetermined threshold. The predetermined threshold may be between −1 and 0.5 or any other suitable value. In one embodiment, the predetermined threshold may be between −1 and 0. As noted above, higher EEG activity in one hemisphere may indicate that the patient is experiencing an ischemic event. Accordingly, if the correlation is low, the method 266 may include determining that the patient is experiencing an ischemic event (block 290) and providing an indication that the patient may be experiencing an ischemic event (block 292). If the correlation is not low, the system 10 may continue to analyze the correlation between depth of anesthesia values for each quadrant of the patient's head (block 262).

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that elements of the disclosed embodiments may be combined or exchanged with one another.

What is claimed is:

1. A medical monitoring system, comprising:
   an electroencephalography (EEG) sensor array comprising a plurality of electrodes configured for EEG monitoring, wherein the plurality of electrodes are configured to be disposed about a patient's head, and wherein the plurality of electrodes comprise a ground electrode, a reference electrode, and a plurality of sensing electrodes; and
   an EEG monitor operatively coupled to the EEG sensor array, wherein the EEG monitor comprises:
      input circuitry configured to receive EEG signals from the plurality of sensing electrodes;
      a processor configured to:
         determine a plurality of depth of anesthesia indices based at least in part on the EEG signals, wherein the depth of anesthesia indices comprise bispectral indices; and
         generate a topographic color map of the depth of anesthesia indices based on a color scale, wherein the color scale comprises a predetermined set of colors, wherein each color of the predetermined set of colors represents a predetermined depth of anesthesia index; and
      a display configured to display the topographic color map;
   wherein the EEG monitor is configured to receive a user selection of one or more regions of the patient's head to monitor, wherein the display is configured to display an anesthesia index for each of the one or more regions, and wherein the processor is configured to determine a correlation between depth of anesthesia indices associated with a first region of the patient's head and depth of anesthesia indices associated with a second region of the patient's head, and wherein the processor is configured to detect a clinically adverse event based at least in part upon the correlation.

2. The system of claim 1, wherein the plurality of electrodes comprises between 64 and 256 electrodes.

3. The system of claim 1, wherein the display is configured to display the color scale associated with the topographic color map.

4. The system of claim 1, wherein the processor is configured to analyze the topographic color map for one or more features or patterns of EEG activity indicative of a clinically adverse event.

5. The system of claim 4, wherein the clinically adverse event comprises a seizure or an ischemic event.

6. The system of claim 4, wherein the EEG monitor is configured to cause the monitor to display an indication of a clinically adverse event in response to a determination that the topographic color map includes the one or more features or patterns of EEG activity indicative of a clinically adverse event.

7. The system of claim 6, wherein the indication identifies a region of the patient's head on the topographic color map that is associated with the detected clinically adverse event.

8. The system of claim 4, wherein the EEG monitor comprises a memory, wherein the memory stores a plurality of reference topographic color maps comprising one or more features or patterns of EEG activity indicative of a clinically adverse event, and wherein the processor is configured to compare the topographic color map to one or more of the stored plurality of reference topographic color maps to detect a clinically adverse event.

9. The system of claim 1, wherein the EEG signals are spontaneous EEG signals.

10. The system of claim 1, wherein the processor is configured to determine a correlation between one or more frequency bands of EEG signals associated with the first region of the patient's head and one or more frequency bands of EEG signals associated with the second region of the patient's head, and wherein the processor is configured to detect a clinically adverse event based at least in part upon the correlation.

11. A method for monitoring a patient, comprising:
   receiving, via an electroencephalograph (EEG) monitor, a plurality of EEG signals from an EEG sensor array, wherein the EEG sensor array comprises a plurality of electrodes configured to be disposed about a patient's head;
   determining, via the EEC monitor, a depth of anesthesia index for each EEG signal of the plurality of EEG signals, wherein the depth of anesthesia index comprises a bispectral index, wherein a first portion of the EEG signals corresponds to a first region of the patient's head and wherein a second portion of the EEG signals corresponds to a second region of the patient's head;
   generating, via the EEG monitor, a topographic color map of depth of anesthesia indices of the first region and depth of anesthesia indices of the second region;
   displaying, via the EEG monitor, the topographic color map; and
   determining, via the EEG monitor, a patient condition based on a correlation between the depth of anesthesia indices of the first region and the depth of anesthesia indices of the second region.

12. The method of claim 11, wherein the plurality of electrodes comprises between 64 and 256 electrodes.

13. The method of claim 11, wherein a third portion and a fourth portion of the EEG signals corresponds to a third region and a fourth region of the patient's head, respectively, and wherein each of the first, second, third, and fourth regions corresponds to a respective quadrant of the patient's head, and wherein a correlation of depth of anesthesia indices between the quadrants is high when delivery of anesthesia to the patient is initiated.

14. The method of claim 13, comprising determining, via the EEG monitor, the patient condition based on a decrease in the correlation of depth of anesthesia indices between the quadrants after a predetermined time has elapsed after the delivery of anesthesia to the patient is initiated.

15. The method of claim 11, wherein determining the patient condition comprises determining a characteristic signature of EEG activity for the plurality of EEG signals.

16. The method of claim 11, wherein the correlation is determined in a time domain.

17. The method of claim 11, wherein the correlation is determined in a frequency domain.

18. An electroencephalography (EEG) monitor, comprising:
- an EEG sensor array;
- input circuitry configured to receive a plurality of EEG signals from the EEG sensor array, wherein the EEG sensor array is configured to be coupled to the EEG monitor and, wherein the EEG sensor array comprises a plurality of electrodes configured to be disposed about a patient's head; and
- a processor configured to:
  - determine a plurality of depth of anesthesia indices based on the received plurality of EEG signals, wherein the depth of anesthesia indices comprise bispectral indices;
  - determine a correlation between depth of anesthesia indices associated with a first region of the patient's head and depth of anesthesia indices associated with a second region of the patient's head;
  - provide an index for the first and second head regions based on the depth of anesthesia indices associated with electrodes disposed on the respective head regions;
  - detect an anesthesia condition of the patient based at least in part upon the index for each head region and on the determined correlation; and
  - provide a user-perceivable indication of the anesthesia condition.

19. The monitor of claim 18, wherein the anesthesia condition comprises ischemia.

20. The monitor of claim 18, wherein the anesthesia condition comprises a seizure.

21. The monitor of claim 18, comprising a display, and wherein the processor is configured to generate a topographic color map of the plurality of depth of anesthesia indices and to cause the monitor to display the topographic color map.

* * * * *